(12) United States Patent
Lightner et al.

(10) Patent No.: US 9,239,875 B2
(45) Date of Patent: *Jan. 19, 2016

(54) METHOD FOR DISAMBIGUATED FEATURES IN UNSTRUCTURED TEXT

(71) Applicant: QBASE, LLC, Reston, VA (US)

(72) Inventors: Scott Lightner, Leesburg, VA (US); Franz Weckesser, Spring Valley, OH (US); Sanjay Boddhu, Dayton, OH (US); Rakesh Dave, Dayton, OH (US); Robert Flagg, Portland, ME (US)

(73) Assignee: QBASE, LLC, Reston, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/557,794

(22) Filed: Dec. 2, 2014

(65) Prior Publication Data

US 2015/0154286 A1    Jun. 4, 2015

Related U.S. Application Data

(60) Provisional application No. 61/910,739, filed on Dec. 2, 2013.

(51) Int. Cl.
*G06F 17/30* (2006.01)
*G06F 19/00* (2011.01)
(Continued)

(52) U.S. Cl.
CPC ...... *G06F 17/30684* (2013.01); *G06F 17/2765* (2013.01); *G06F 17/30705* (2013.01); *G06F 19/24* (2013.01); *G06F 19/707* (2013.01)

(58) Field of Classification Search
CPC .......... G06F 17/30598; G06F 17/30705; G06F 19/24; G06F 19/707
See application file for complete search history.

(56) References Cited

U.S. PATENT DOCUMENTS 6,128,660 A    10/2000    Grimm et al.
6,178,529 B1    1/2001    Short et al.
(Continued)

FOREIGN PATENT DOCUMENTS

WO    2013/003770 A2    1/2013

OTHER PUBLICATIONS

International Search Report and Written Opinion dated Feb. 24, 2015 corresponding to International Patent Application No. PCT/US2014/067918, 10 pages.

(Continued)

*Primary Examiner* — Miranda Huang
(74) *Attorney, Agent, or Firm* — Eric L. Sophir; Dentons US LLP (57) ABSTRACT

A method for disambiguating features in unstructured text is provided. The disclosed method may not require pre-existing links to be present. The method for disambiguating features in unstructured text may use co-occurring features derived from both the source document and a large document corpus. The disclosed method may include multiple modules, including a linking module for linking the derived features from the source document to the co-occurring features of an existing knowledge base. The disclosed method for disambiguating features may allow identifying unique entities from a knowledge base that includes entities with a unique set of co-occurring features, which in turn may allow for increased precision in knowledge discovery and search results, employing advanced analytical methods over a massive corpus, employing a combination of entities, co-occurring entities, topic IDs, and other derived features.

20 Claims, 8 Drawing Sheets

(51) Int. Cl.
*G06F 19/24* (2011.01)
*G06F 17/27* (2006.01)

(56) References Cited

U.S. PATENT DOCUMENTS

| | | |
|---|---|---|
| 6,266,781 B1 | 7/2001 | Chung et al. |
| 6,353,926 B1 | 3/2002 | Parthesarathy et al. |
| 6,738,759 B1 | 5/2004 | Wheeler et al. |
| 6,832,373 B2 | 12/2004 | O'Neill |
| 7,058,846 B1 | 6/2006 | Kelkar et al. |
| 7,370,323 B2 | 5/2008 | Marinelli et al. |
| 7,421,478 B1 | 9/2008 | Muchow |
| 7,447,940 B2 | 11/2008 | Peddada |
| 7,543,174 B1 | 6/2009 | van Rietschote et al. |
| 7,681,075 B2 | 3/2010 | Havemose et al. |
| 7,818,615 B2 | 10/2010 | Krajewski et al. |
| 7,899,871 B1 | 3/2011 | Kumar et al. |
| 8,055,933 B2 | 11/2011 | Jaehde et al. |
| 8,122,026 B1 | 2/2012 | Laroco et al. |
| 8,341,622 B1 | 12/2012 | Eatough |
| 8,345,998 B2 | 1/2013 | Malik et al. |
| 8,356,036 B2 | 1/2013 | Bechtel et al. |
| 8,375,073 B1 | 2/2013 | Jain |
| 8,423,522 B2 | 4/2013 | Lang et al. |
| 8,429,256 B2 | 4/2013 | Vidal et al. |
| 8,726,267 B2 | 5/2014 | Li et al. |
| 8,782,018 B2 | 7/2014 | Shim et al. |
| 8,995,717 B2 | 3/2015 | Cheng et al. |
| 9,009,153 B2 | 4/2015 | Khan et al. |
| 9,025,892 B1 | 5/2015 | Lightner et al. |
| 9,032,387 B1 | 5/2015 | Hill et al. |
| 2001/0037398 A1 | 11/2001 | Chao et al. |
| 2002/0165847 A1 | 11/2002 | McCartney et al. |
| 2002/0174138 A1 | 11/2002 | Nakamura |
| 2003/0028869 A1 | 2/2003 | Drake et al. |
| 2003/0112792 A1 | 6/2003 | Cranor et al. |
| 2003/0158839 A1 | 8/2003 | Faybishenko et al. |
| 2003/0182282 A1 | 9/2003 | Ripley |
| 2004/0027349 A1 | 2/2004 | Landau et al. |
| 2004/0049478 A1* | 3/2004 | Jasper ............. G06F 17/30705 |
| 2004/0143571 A1 | 7/2004 | Bjornson et al. |
| 2004/0153869 A1 | 8/2004 | Marinelli et al. |
| 2004/0205064 A1 | 10/2004 | Zhou et al. |
| 2004/0215755 A1 | 10/2004 | O'Neill |
| 2005/0192994 A1 | 9/2005 | Caldwell et al. |
| 2006/0101081 A1 | 5/2006 | Lin et al. |
| 2006/0294071 A1 | 12/2006 | Weare et al. |
| 2007/0005639 A1 | 1/2007 | Gaussier et al. |
| 2007/0203693 A1 | 8/2007 | Estes |
| 2007/0203924 A1 | 8/2007 | Guha et al. |
| 2007/0240152 A1 | 10/2007 | Li et al. |
| 2007/0250519 A1 | 10/2007 | Fineberg et al. |
| 2007/0282959 A1 | 12/2007 | Stern |
| 2008/0010683 A1 | 1/2008 | Baddour et al. |
| 2008/0027920 A1 | 1/2008 | Schipunov et al. |
| 2009/0019013 A1 | 1/2009 | Tareen et al. |
| 2009/0043792 A1 | 2/2009 | Barsness et al. |
| 2009/0049038 A1 | 2/2009 | Gross |
| 2009/0089626 A1 | 4/2009 | Gotch et al. |
| 2009/0094484 A1 | 4/2009 | Son et al. |
| 2009/0240682 A1 | 9/2009 | Balmin et al. |
| 2009/0292660 A1 | 11/2009 | Behal et al. |
| 2009/0299999 A1 | 12/2009 | Loui et al. |
| 2009/0322756 A1 | 12/2009 | Robertson et al. |
| 2010/0077001 A1 | 3/2010 | Vogel et al. |
| 2010/0138931 A1 | 6/2010 | Thorley et al. |
| 2010/0223264 A1 | 9/2010 | Brucker et al. |
| 2010/0235311 A1* | 9/2010 | Cao et al. ................ 706/46 |
| 2010/0274785 A1 | 10/2010 | Procopiuc et al. |
| 2011/0071975 A1 | 3/2011 | Friedlander et al. |
| 2011/0093471 A1 | 4/2011 | Brockway et al. |
| 2011/0119243 A1 | 5/2011 | Diamond et al. |
| 2011/0125764 A1 | 5/2011 | Carmel et al. |
| 2011/0282888 A1* | 11/2011 | Koperski .......... G06F 17/30864 707/752 |
| 2011/0296397 A1 | 12/2011 | Vidal et al. |
| 2012/0030220 A1 | 2/2012 | Edwards et al. |
| 2012/0059839 A1 | 3/2012 | Andrade et al. |
| 2012/0102121 A1* | 4/2012 | Wu et al. ................ 709/206 |
| 2012/0117069 A1 | 5/2012 | Kawanishi et al. |
| 2012/0131139 A1 | 5/2012 | Siripurapu et al. |
| 2012/0246154 A1 | 9/2012 | Duan et al. |
| 2012/0310934 A1 | 12/2012 | Peh et al. |
| 2012/0323839 A1 | 12/2012 | Kiciman et al. |
| 2013/0132405 A1 | 5/2013 | Bestgen et al. |
| 2013/0166480 A1 | 6/2013 | Popescu et al. |
| 2013/0166547 A1 | 6/2013 | Pasumarthi et al. |
| 2013/0290232 A1 | 10/2013 | Tsytsarau et al. |
| 2013/0303198 A1 | 11/2013 | Sadasivam et al. |
| 2014/0013233 A1 | 1/2014 | Ahlberg et al. |
| 2014/0022100 A1 | 1/2014 | Fallon et al. |
| 2014/0156634 A1 | 6/2014 | Buchmann et al. |
| 2014/0244550 A1 | 8/2014 | Jin et al. |
| 2014/0280183 A1* | 9/2014 | Brown .............. G06F 17/30321 707/741 |
| 2014/0351233 A1 | 11/2014 | Crupi et al. |
| 2015/0074037 A1 | 3/2015 | Sarferaz |
| 2015/0154079 A1 | 6/2015 | Lightner et al. |
| 2015/0154264 A1 | 6/2015 | Lightner et al. |
| 2015/0154297 A1 | 6/2015 | Lightner et al. |

OTHER PUBLICATIONS

International Search Report and Written Opinion dated Mar. 6, 2015 corresponding to International Patent Application No. PCT/US2014/067993, 9 pages.

International Search Report and Written Opinion of the International Searching Authority dated Mar. 3, 2015 corresponding to International Patent Application No. PCT/US2014/067921, 10 pages.

International Search Report and Written Opinion of the International Searching Authority dated Apr. 15, 2015 corresponding to International Patent Application No. PCT/US2014/068002, 10 pages.

International Search Report and Written Opinion dated Mar. 10, 2015 corresponding to International Patent Application No. PCT/US2014/067999, 10 pages.

Tunkelang, D., "Faceted Search," Morgan & Claypool Publ., 2009, pp. i-79.

Schuth, A., et al., "University of Amsterdam Data Centric Ad Hoc and Faceted Search Runs," ISLA, 2012, pp. 155-160.

Tools, Search Query Suggestions using ElasticSearch via Shingle Filter and Facets, Nov. 2012, pp. 1-12.

* cited by examiner

$J$ = number of multi-document components.
$V^{(j)}$ = number of terms in the vocabulary of the $j$th component.
$D$ = number of documents.
$N$ = number of tokens in (a component) of a document (actually depends on both $j$ and $d$).
$K$ = number of topics.
$\alpha$ = hyperparameter on the mixing proportions ($K$-vector or scalar if symmetric).
$\eta^{(j)}$ = hyperparameter on the mixture components ($V^{(j)}$-vector or scalar if symmetric).
$\theta_d$ = the topic mixture proportion for document $d$.
$\phi_k^{(j)}$ = mixture component for the $j$the component of the $k$th topic.
$z_{d,n}^{(j)}$ = mixture indicator that chooses the topic for the $n$th word in $j$th component of document $d$
$w_{d,n}^{(j)}$ = term indicator for the $n$th word in $j$th component of document $d$

FIG. 5

$$p(z_i^{(j)} = k | w_i^{(j)} = t, z_{-i}^{(j)}, z^{(-j)}, w_{-i}^{(j)}, w^{(-j)}, \alpha, \eta) \propto \frac{n_{d,-i}^{(j,k)} + \alpha}{\sum_{k'=1}^{K}(n_{d,-i}^{(j,k')} + \alpha)} \cdot \frac{n_{k,-i}^{(j,t)} + \beta^{(j)}}{\sum_{t'=1}^{V_j}(n_{k,-i}^{(j,t')} + \beta^{(j)})}$$

$$E\{\phi_{k,t}^{(j)} | z^{(j)}, w^{(j)}, \beta\} = \frac{n_k^{(j,t)} + \beta^{(j)}}{\sum_{t'=1}^{V_j}(n_k^{(j,t')} + \beta^{(j)})}$$

$$E\{\theta_{d,k} | z^{(1)}, \ldots, z^{(J)}, \alpha\} = \frac{\sum_{j=1}^{J}(n_d^{(j,k)} + \alpha)}{\sum_{k=1}^{K} \sum_{j=1}^{J}(n_d^{(j,k)} + \alpha)}$$

$J$ = number of multi-document components.

$V^{(j)}$ = number of terms in the vocabulary of the $j$th component.

$K$ = number of topics.

$\alpha$ = hyperparameter on the mixing proportions ($K$-vector or scalar if symmetric).

$\eta$ = hyperparameter on the mixture components (actually, $J$ vectors of length $V^{(j)}$, respectively).

$\theta_d$ = the topic mixture proportion for document $d$.

$\phi_k^{(j)}$ = mixture component for the $j$the component of the $k$th topic.

$z_{d,n}^{(j)}$ = mixture indicator that chooses the topic for the $n$th word in $j$th component of document $d$.

$w_{d,n}^{(j)}$ = term indicator for the $n$th word in $j$th component of document $d$.

$n_d^{(j,k)}$ = the number of terms in component $j$ of document $d$ assigned to topic $k$.

$n_k^{(j,t)}$ = the number of times term $t$ was assigned to topic $k$ on in component $j$ of the corpus.

FIG. 6

Algorithm 1 Stochastic Variational Inference for MC-TM

1: Set $\epsilon = 0.00001$
2: Define $\rho_t := (\tau_0 + t)^{-\kappa}$
3: Initialize $\lambda$ randomly.
4: for $t = 0$ to $\infty$ do
5:    *E-Step:*
6:    Initialize $\gamma_{tk} = 1$. (The constant 1 is arbitrary.)
7:    repeat
8:       Set $\phi_{twk}^{(j)} \propto e^{E_q[\log \theta_{tk}] + E_q[\log \beta_{kw}^{(j)}]}$
9:       Set $\gamma_{tk} = \alpha + \sum_{j=1}^{J} \sum_{w=1}^{W^{(j)}} \phi_{twk}^{(j)} n_{tw}^{(j)}$
10:    until $\frac{1}{K}\sum_k |\Delta \gamma_{tk}| < \epsilon$
11:    *M-Step:*
12:    Compute $\hat{\lambda}_{k,w}^{(j)} = \eta^{(j)} + D \cdot n_{t,w}^{(j)} \cdot \phi_{t,w,k}^{(j)}$
13:    Set $\lambda = (1 - \rho_t)\lambda + \rho_t \hat{\lambda}$
14: end-for $\alpha$ = hyperparameter on the document-topic mixing proportions.
$\eta$ = hyperparameter on the topic-term mixture proportions.
$\phi_{d,n}$ = parameter for the multinomial distribution of topic assignments in document $d$.
$\gamma_d$ = parameter for the Dirichlet distribution on document-topic proportions for document $d$.
$\lambda_k$ = parameter for the Dirichlet distribution on topic-term proportions for topic $k$.

FIG. 7

| | |
|---|---|
| Tokens | album, music, song, released, songs, single, albums, love, tour, first ... |
| Key Phrases | album, song, music, rock, debut_album, studio_album, solo_album, edit, music_video, guitar ... |
| Organizations | mtv, beatles, rolling_stone, youtube, emi, warner_bros, rca, official_charts_company, rovi_corporation, atlantic_records ... |
| Persons | britney_spears, bruce_springsteen, robin_thicke, bob_dylan, mariah_carey, john_lennon, jennifer_lopez, stevie_nicks, melissa_etheridge, dylan ... |
| Locations | us, united_states, uk, united_kingdom, united_states_of_america, u_s, australia, glastonbury ... |

FIG. 8

METHOD FOR DISAMBIGUATED FEATURES IN UNSTRUCTURED TEXT

CROSS-REFERENCE TO RELATED APPLICATIONS

This application claims the benefit of U.S. Provisional Application No. 61/910,739, entitled "Method For Disambiguating Features In Unstructured Text," filed on Dec. 2, 2013, which is incorporated herein by reference in its entirety.

This application is related to U.S. patent application Ser. No. 14/558,300, entitled "EVENT DETECTION THROUGH TEXT ANALYSIS USING TRAINED EVENT TEMPLATE MODELS," filed Dec. 2, 2014; and U.S. patent application Ser. No. 14/558,254, entitled "DESIGN AND IMPLEMENTATION OF CLUSTERED IN-MEMORY DATABASE," filed Dec. 2, 2014; each of which are incorporated herein by reference in their entirety.

TECHNICAL FIELD

The present disclosure generally relates to data management; and, more specifically, to data management systems and methods that extract and store material from source items received over a network.

BACKGROUND

Searching for information about entities (i.e., people, locations, organizations) in large document collection, including sources such as a network, may often be ambiguous, which may lead to imprecise text processing functions, imprecise association of features during knowledge extraction, and, thus, imprecise data analysis.

State of the art systems use linkage based clustering and ranking in several algorithms, such as PageRank and the hyperlink-induced topic search (HITS) algorithm. The basic idea behind this and related approaches is that pre-existing links typically exist between related pages or concepts. A limitation of clustering-based techniques is that sometimes contextual information needed to disambiguate entities is not present in the context, leading to incorrectly disambiguated results. Similarly, documents about different entities in the same or superficially similar contexts may be incorrectly clustered together.

Other systems attempt to disambiguate entities by reference to one or more external dictionaries (or knowledgebase) of entities. In such systems, an entity's context is compared to possible matching entities in the dictionary and the closest match is returned. A limitation associated with current dictionary-based techniques stems from the fact that entities may increase in number at any moment and, therefore, no dictionary may include a representation of all of the world's entities. Thus, if a document's context is matched to an entity in the dictionary, then the technique has identified only the most similar entity in the dictionary, and not necessarily the correct entity, which may be outside the dictionary.

Most methods just use entities and key phrases in the disambiguation process. Therefore, there is still a need for accurate entity disambiguation techniques that allow a precise data analysis.

SUMMARY

Some embodiments describe a method for disambiguating features. The method may include multiple modules, such as one or more feature extraction modules, one or more disambiguation modules, one or more scoring modules, and one or more linking modules.

Disambiguating features will be supported in part by extracting topics from the ambient document of the feature, employing a multi-component extension of Latent Dirichlet Allocation (MC-LDA) topic models. Here, each component is modeled around each secondary feature stored in the existing knowledge base or extracted on the incoming document. Further, the linking or disambiguation process is modeled as topic inference from the MC-LDA, which provides automated weight estimation during the MC-LDA training and applies them readily during inference.

The exemplary method may improve the accuracy of entity disambiguation beyond what may be achieved by considering no document linking Taking account of document linkage may allow better disambiguation by considering document and entity relationships implied by links.

In one embodiment, a method comprises searching, by a node of a system hosting an in-memory database, a set of candidate records to identify one or more candidates matching one or more extracted features, wherein an extracted feature that matches a candidate is a primary feature; associating, by the node, each of the extracted features with one or more machine-generated topic identifiers ("topic IDs"); disambiguating, by the node, each of the primary features from one another based on relatedness of topic IDs; identifying, by the node, a set of secondary features associated with each primary feature based upon the relatedness of topic IDs; disambiguating, by the node, each of the primary features from each of the secondary features in the associated set of secondary features based on relatedness of topic IDs; linking, by the node, each primary feature to the associated set of secondary features to form a new cluster; determining, by the node, whether the new cluster matches an existing knowledgebase cluster, wherein, when there is a match, determining, by the disambiguation module of the in-memory database server computer, an existing unique identifier ("unique ID") corresponding to each matching primary feature in the knowledgebase cluster and updating the knowledgebase cluster to include the new cluster; and when there is no match, creating, by the node, a new knowledgebase cluster and assigning a new unique ID to the primary feature of the new knowledgebase cluster; and transmitting, by the node, one of the existing unique ID and the new unique ID for the primary feature.

In another embodiment, a non-transitory computer readable medium having stored thereon computer executable instructions comprises searching, by a node of a system hosting an in-memory database, a set of candidate records to identify one or more candidates matching one or more extracted features, wherein an extracted feature that matches a candidate is a primary feature; associating, by the node, each of the extracted features with one or more machine-generated topic identifiers ("topic IDs"); disambiguating, by the node, each of the primary features from one another based on relatedness of topic IDs; identifying, by the node, a set of secondary features associated with each primary feature based upon the relatedness of topic IDs; disambiguating, by the node, each of the primary features from each of the secondary features in the associated set of secondary features based on relatedness of topic IDs; linking, by the node, each primary feature to the associated set of secondary features to form a new cluster; determining, by the node, whether the new cluster matches an existing knowledgebase cluster, wherein, when there is a match, determining, by the node, an existing unique identifier ("unique ID") corresponding to each matching primary feature in the knowledgebase cluster and updating the knowledgebase cluster to include the new cluster; and when there is no match, creating a new knowledgebase cluster and assigning a new unique ID to the primary feature of the new knowledgebase cluster; and transmitting, by the node, one of the existing unique ID and the new unique ID for the primary feature.

Additional features and advantages of an embodiment will be set forth in the description which follows, and in part will be apparent from the description. The objectives and other advantages of the invention will be realized and attained by the structure particularly pointed out in the exemplary embodiments in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The present disclosure can be better understood by referring to the following figures. The accompanying drawings constitute a part of this specification and illustrate an embodiment of the invention and together with the specification, explain the invention. The components in the figures are not necessarily to scale, emphasis instead being placed upon illustrating the principles of the disclosure. In the figures, reference numerals designate corresponding parts throughout the different views.

DEFINITIONS

As used herein, the following terms may have the following definitions:

"Document" refers to a discrete electronic representation of information having a start and end.

"Multi-Document" refers to a document with its tokens, different types of named entities, and key phrases organized into separate "bag-of-surface-forms" components.

"Database" refers to any system including any combination of clusters and modules suitable for storing one or more collections and suitable to process one or more queries.

"Corpus" refers to a collection of one or more documents.

"Live corpus", or "Document Stream", refers to a corpus that is constantly fed as new documents are uploaded into a network.

"Feature" refers to any information which is at least partially derived from a document.

"Feature attribute" refers to metadata associated with a feature; for example, location of a feature in a document, confidence score, among others.

"Cluster" refers to a collection of features.

"Entity knowledge base" refers to a base containing features/entities.

"Link on-the-fly module" refers to any linking module that performs data linkage as data is requested from the system rather than as data is added to the system.

"Memory" refers to any hardware component suitable for storing information and retrieving said information at a sufficiently high speed.

"Module" refers to a computer software component suitable for carrying out one or more defined tasks.

"Sentiment" refers to subjective assessments associated with a document, part of a document, or feature.

"Topic" refers to a set of thematic information which is at least partially derived from a corpus.

"Topic Identifier", or "topic ID", refers to an identifier that refers to a specific instance of a topic.

"Topic Collection" refers to a specific set of topics derived from the corpus, with each topic having a unique identifier ("unique ID").

"Topic Classification" refers to the assignation of specific topic identifiers as features of a document.

"Query" refers to a request to retrieve information from one or more suitable databases.

DETAILED DESCRIPTION

Reference will now be made in detail to the preferred embodiments, examples of which are illustrated in the accompanying drawings. The embodiments described above are intended to be exemplary. One skilled in the art recognizes that numerous alternative components and embodiments may be substituted for the particular examples described herein and still fall within the scope of the invention.

The present disclosure describes a method for disambiguating features in an unstructured text. Although the exemplary embodiments discuss practices for disambiguating features according to this disclosure, it is intended that the systems and methods described herein can be configured for any suitable use within the scope of this disclosure.

Existing knowledge bases include non-ambiguous features and their related features, which may lead to low confidence text analytics. An aspect of the present disclosure includes a method that may allow an increased accuracy in feature and entity disambiguation, therefore, increased accuracy in text analytics.

According to an embodiment, the disclosed method for disambiguating features may be employed in an initial corpus of data to perform a document ingestion and a feature extraction that may allow a topic classification and other text analytics on each document included in the initial corpus. Each feature may be identified and recorded as name, type, positional information in the document, and confidence score, among others.

Figure 1:
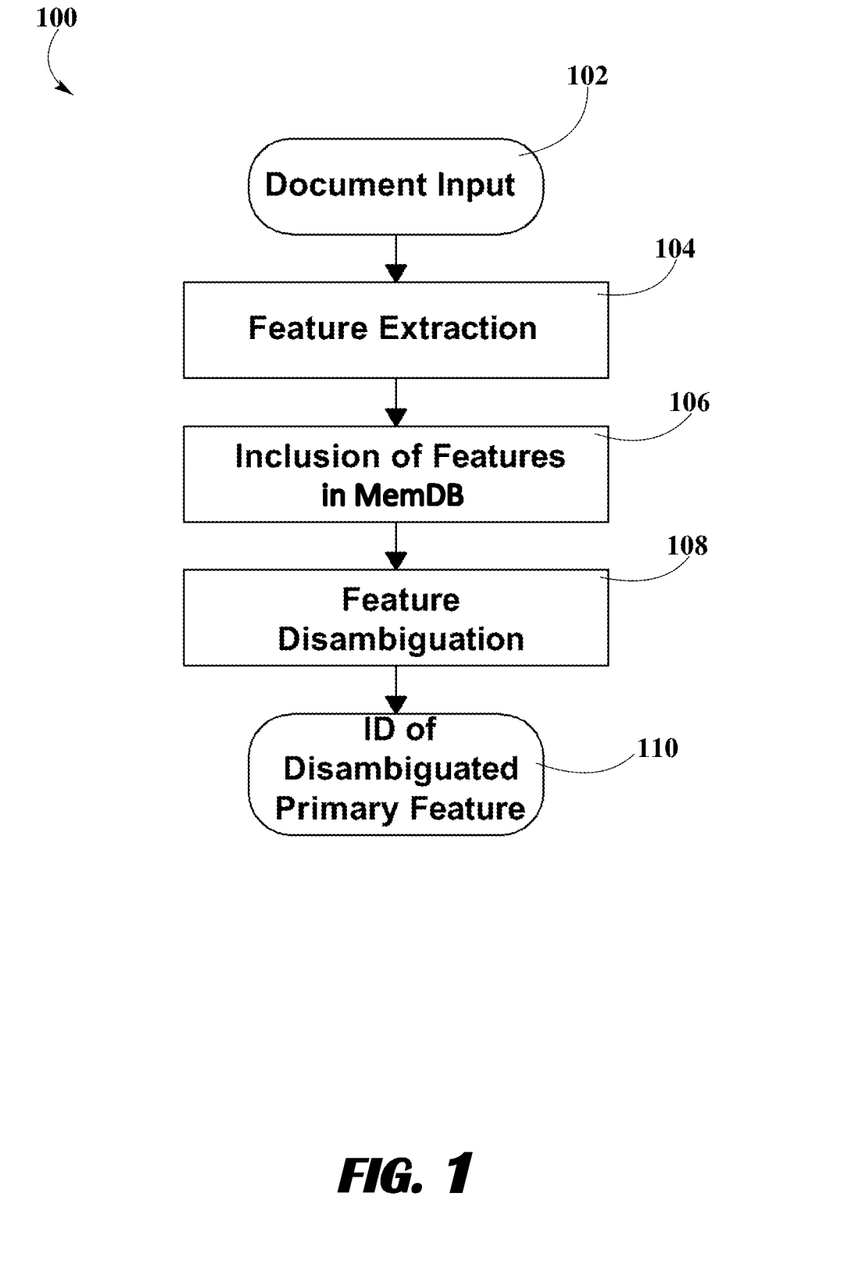
FIG. 1 is a flowchart of a method for disambiguating features in unstructured text, according to an exemplary embodiment.

FIG. 1 is a flowchart of a method 100 illustrating a plurality of steps for disambiguating features in unstructured text. According to an embodiment, method 100 for disambiguating features may initiate as a new document input, step 102, is made in an existing knowledge base. Subsequently, a feature extraction step 104 may be performed on the document. According to an embodiment, a feature may be related to different feature attributes, such as a topic identifier ("topic ID"), a document identifier ("document ID"), feature type, feature name, confidence score, and feature position, among others.

According to various embodiments, document input in step 102 may be fed from a massive corpus or live corpus (such as the internet or network connected corpus) that in turn, may be fed every second.

According to different embodiments, one or more feature recognition and extraction algorithms may be employed during feature extraction step 104 to analyze the unstructured text of document input step 102. A score may be assigned to each extracted feature. The score may indicate the level of certainty of the feature being correctly extracted with the correct attributes.

Additionally, during feature extraction step 104, one or more primary features may be identified from a document input in step 102. Each primary feature may have been associated with a set of feature attributes and one or more secondary features. Each secondary feature may be associated with a set of feature attributes. In some embodiments, one or more secondary features may have one or more tertiary features, each one having its own set of feature attributes.

Taking into account the feature attributes, the relative weight or relevance of each of the features within document input at step 102 may be determined. Additionally, the relevance of the association between features may be determined using a weighted scoring model.

Following feature extraction step 104, the features extracted from document input at step 102 and all their related information may be loaded into an in-memory data base (MemDB), during inclusion of features in MemDB, step 106, as part of a feature disambiguation request step 108.

In an embodiment, the MemDB forms part of a disambiguation computer server environment having one or more processors executing the steps discussed in connection with FIGS. 1-8. In one embodiment, the MemDB is a computer module that may include one or more search controllers, multiple search nodes, collections of compressed data, and a disambiguation sub module. One search controller may be selectively associated with one or more search nodes. Each search node may be capable of independently performing a fuzzy key search through a collection of compressed data and returning a set of scored results to its associated search controller.

Feature disambiguation step 108 may be performed by a disambiguation sub module within the MemDB. Feature disambiguation 108 process may include machine generated topic IDs, which may be employed to classify features, documents, or corpora. The relatedness of individual features and specific topic IDs may be determined using disambiguating algorithms. In some documents, the same feature may be related to one or more topic IDs, depending on the context of the different occurrences of the feature within the document.

The set of features (like topics, proximity terms and entities, key phrases, events and facts) extracted from one document may be compared with sets of features from other documents, using disambiguating algorithms to define with a certain level of accuracy if two or more features across different documents are a single feature or if they are distinct features. In some examples, co-occurrence of two or more features across the collection of documents in the database may be analyzed to improve the accuracy of feature disambiguation process 108. In some embodiments, global scoring algorithms may be used to determine the probability of features being the same.

In some embodiments, as part of the feature disambiguation process 108, a knowledge base may be generated within the MemDB. This knowledge base may be used to temporarily store clusters of relevant disambiguated primary features and their related secondary features. When new documents are loaded into the MemDB, the new disambiguated set of features may be compared with the existing knowledge base in order to determine the relationship between features and determine if there is a match between the new features and already extracted features.

If the features compared match, the knowledge base may be updated and a feature ID of the matching features may be returned to the user and/or requesting application or process and further based on the frequency of matches a prominence measure could be attached with the feature ID, which captures its popularity index in the given corpus. If the features compared do not match with any of the already extracted features, a unique feature ID is assigned to the disambiguated entity or feature, and the unique feature ID is associated with the cluster of defining features and stored in within the knowledge base of the MemDB. Subsequently, in step 110, the feature ID of disambiguated feature may be returned to the source through the system interface. In some embodiments, the feature ID of disambiguated feature may include secondary features, cluster of features, relevant feature attributes or other requested data. Disambiguation sub module employed for feature disambiguation step 108 is described in more detail in FIG. 2 below.

Disambiguation Sub Module

Figure 2:
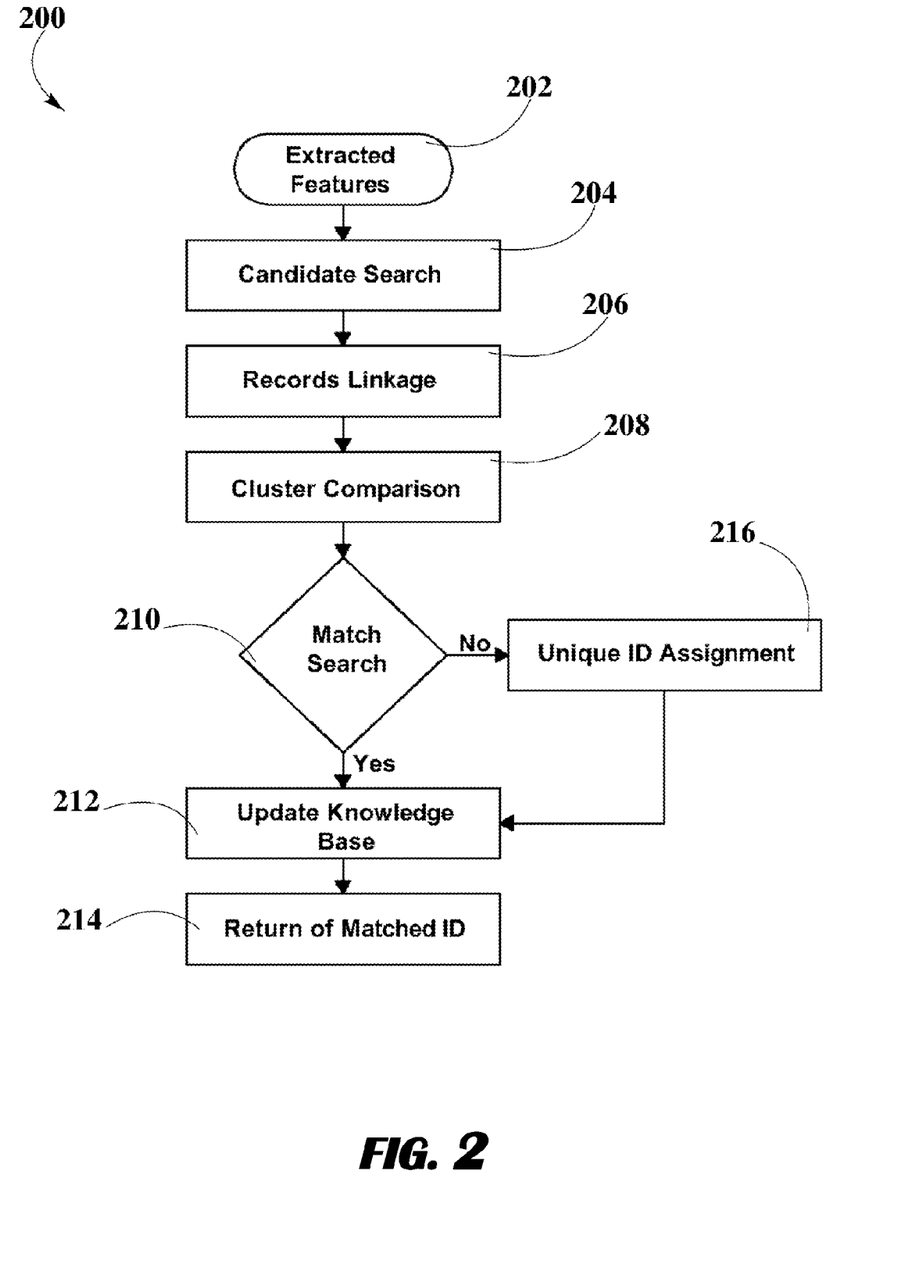
FIG. 2 is a flowchart of the steps performed by a disambiguation module employed in the method for disambiguating features, according to an exemplary embodiment.

FIG. 2 is a flowchart of a process 200 performed by a disambiguation sub module employed in unstructured texts for feature disambiguation step 108 of the method 100 (FIG. 1), according to an embodiment. Disambiguation process 200 may begin after inclusion of features in MemDB in step 106 of FIG. 1. The extracted features provided in step 202 may be used to perform a candidate search in step 204, in which a search for the extracted features may be performed through all candidate records, including co-occurring features.

According to various embodiments, candidates may be primary features with a set of associated secondary features that may be used in feature disambiguation process 108.

The disambiguation results may be improved by the co-occurrence of topic IDs and relatedness among topic IDs. The relatedness of topic IDs, even across different topic models can be discovered from a large corpus where the topic IDs have been assigned. Related topic IDs can be used during records linkage step 206 to provide linkage to documents that may not contain the exact topic ID but do contain one or more related topic IDs. This approach may improve the recall of relevant features to be included in the records linkage step 206 and improve disambiguation results in certain cases.

Once sets of potentially related documents have been identified and sets of relevant primary and secondary features within these documents have been extracted, feature attributes, the relationships between features of the same document (meaningful context), the relative weight of the features and other variables may be used during records linkage process 206, to disambiguate primary and secondary features across documents. Then, each of the records may be linked to other records to determine clusters of disambiguated primary features and their related secondary features. The algorithms used for records linkage 206 may be capable of overcoming spelling errors or transliterations and other challenges of mining unstructured data sets.

Cluster comparison step 208 may include the assignment of relative matching scores to clusters of disambiguated features, different thresholds of acceptance may be defined for different applications. The defined levels of accuracy may determine which scores may be considered a positive match search and which scores may be considered a negative match search, step 210. Each new cluster may be given a unique ID and may be temporarily stored in a knowledge base. Each new cluster may include a new disambiguated primary feature and its set of secondary features. If a new cluster matches a cluster that is already stored in the knowledge base, the system updates knowledge base in step 212, and return of a matched feature ID to the user and/or requesting application or process may be performed in step 214. Update of knowledge base 212 may imply the association of additional of secondary features to one primary feature, or the addition of feature attributes that were not previously associated with primary or secondary features.

If the cluster being evaluated is assigned a score below the threshold of positive match search 210, the system performs a unique ID assignment, step 216, to the primary feature of the cluster and updates knowledge base 212. Afterwards, the system performs a return of matched ID process 214. Records linkage step 206 is further explained in detail in FIG. 3.

Link On-the-Fly Sub Module

Figure 3:
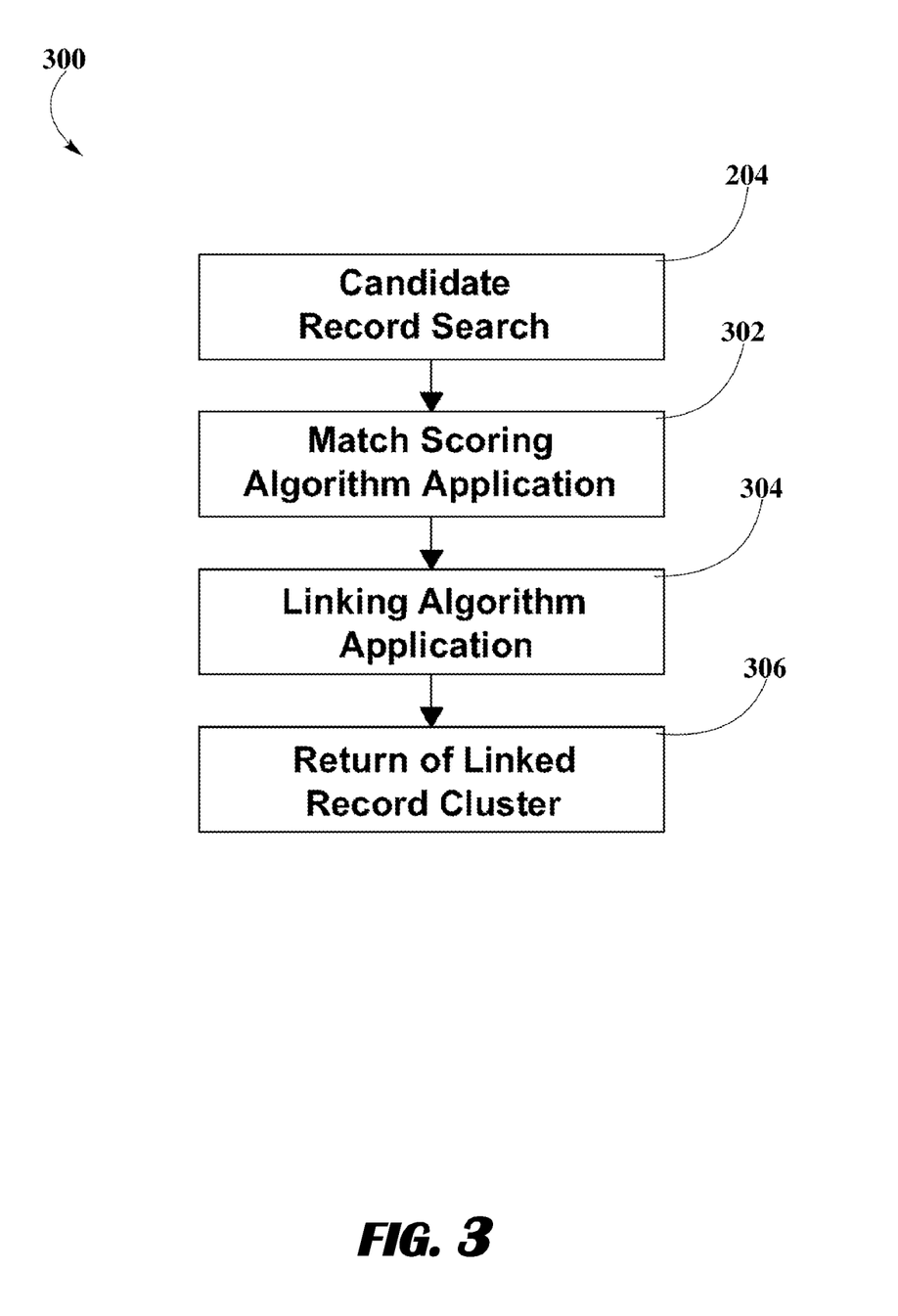
FIG. 3 is a flowchart of the steps performed by a link on-the-fly module employed in the method for disambiguating features, according to an exemplary embodiment.

FIG. 3 is a flowchart of a process 300 performed by a link on-the-fly ("link OTF") sub module employed in method 100 for disambiguating features, according to an embodiment. Link OTF process 300 may be capable of constantly evaluating, scoring, linking, and clustering a feed of information. Link OTF sub module may perform records linkage 206 using multiple algorithms. Candidate search results of step 204 may be constantly fed into link OTF module 300. The input of data may be followed by a match scoring algorithm application, step 302, where one or more match scoring algorithms may be applied simultaneously in multiple search nodes of the MemDB while performing fuzzy key searches for evaluating and scoring the relevant results, taking in account multiple feature attributes, such as string edit distances, phonetics, and sentiments, among others.

Afterwards, a linking algorithm application step 304 may be added to compare all candidate records, identified during match scoring algorithm application step 302, to each other. Linking algorithm application 304 may include the use of one or more analytical linking algorithms capable of filtering and evaluating the scored results of the fuzzy key searches performed inside the multiple search nodes of the MemDB. In some examples, co-occurrence of two or more features across the collection of identified candidate records in the MemDB may be analyzed to improve the accuracy of the process. Different weighted models and confidence scores associated with different feature attributes may be taken into account for linking algorithm application 304.

After the linking algorithm application step 304, the linked results may be arranged in clusters of related features and returned, as part of return of linked records clusters in step 306.

Figure 4:
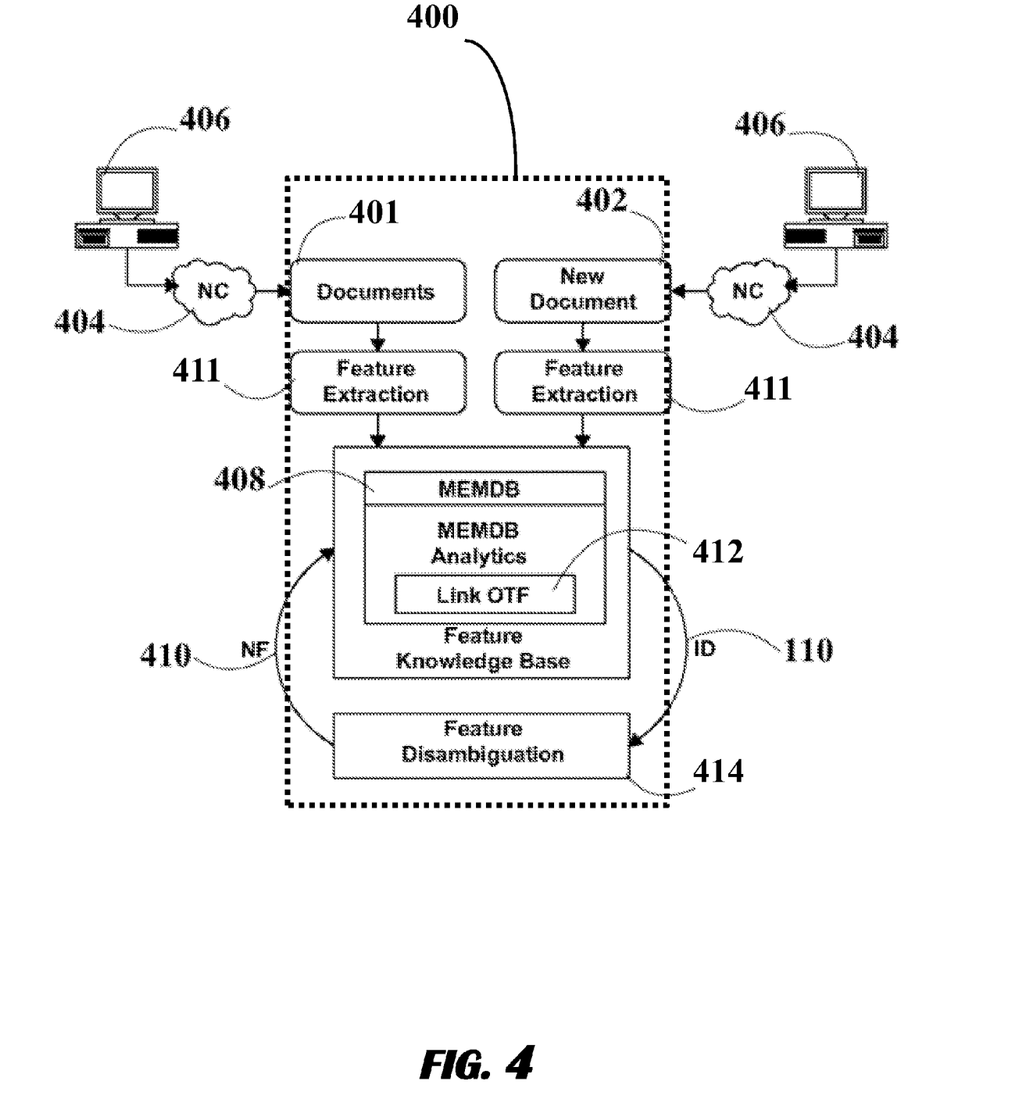
FIG. 4 is an illustrative diagram of a system employed for implementing the method for disambiguating features, according to an exemplary embodiment.

FIG. 4 is an illustrative diagram of an embodiment of a system 400 for disambiguating features in unstructured text, as discussed above in connection with FIG. 1. The system 400 hosts an in-memory database and comprises one or more nodes.

According to an embodiment, the system 400 includes one or more processors executing computer instructions for a plurality of special-purpose computer modules 401, 402, 411, 412, and 414 (discussed below) to disambiguate features within one or more documents. As shown in FIG. 4, the document input modules 401, 402 receive documents from internet based sources and/or a live corpus of documents. A large number of new documents may be uploaded by the second into the document input module 402 through a network connection 404. Therefore, the source may be constantly getting new knowledge, updated by user workstations 406, where such new knowledge is not pre-linked in a static way. Thus, the number of documents to be evaluated may be infinitely increasing.

This evaluation may be achieved via the MemDB computer 408. MemDB 408 may facilitate a faster disambiguation process, may facilitate disambiguation process on-the-fly, which may facilitate reception of the latest information that is going to contribute to MemDB 408. Various methods for linking the features may be employed, which may essentially use a weighted model for determining which entity types are most important, which have more weight, and, based on confidence scores, determine how confident the extraction and disambiguation of the correct features has been performed, and that the correct feature may go into the resulting cluster of features. As shown in FIG. 4, as more system nodes are working in parallel, the process may become more efficient.

According to various embodiments, when a new document arrives into the system 400 via the document input module 401, 402 through a network connection 404, feature extraction is performed via the extraction module 411 and, then, feature disambiguation may be performed on the new document via the feature disambiguation sub-module 414 of the MemDB 408. In one embodiment, after feature disambiguation of the new document is performed, the extracted new features 410 may be included in the MemDB to pass through link OTF sub-module 412; where the features may be compared and linked, and a feature ID of disambiguated feature 110 may be returned to the user as a result from a query. In addition to the feature ID, the resulting feature cluster defining the disambiguated feature may optionally be returned.

MemDB computer 408 can be a database storing data in records controlled by a database management system (DBMS) (not shown) configured to store data records in a device's main memory, as opposed to conventional databases and DBMS modules that store data in "disk" memory. Conventional disk storage requires processors (CPUs) to execute read and write commands to a device's hard disk, thus requiring CPUs to execute instructions to locate (i.e., seek) and retrieve the memory location for the data, before performing some type of operation with the data at that memory location. In-memory database systems access data that is placed into main memory, and then addressed accordingly, thereby mitigating the number of instructions performed by the CPUs and eliminating the seek time associated with CPUs seeking data on hard disk.

In-memory databases may be implemented in a distributed computing architecture, which may be a computing system comprising one or more nodes configured to aggregate the nodes' respective resources (e.g., memory, disks, processors). As disclosed herein, embodiments of a computing system hosting an in-memory database may distribute and store data records of the database among one or more nodes. In some embodiments, these nodes are formed into "clusters" of nodes. In some embodiments, these clusters of nodes store portions, or "collections," of database information.

Various embodiments provide a computer executed feature disambiguation technique that employs an evolving and efficiently linkable feature knowledge base that is configured to store secondary features, such as co-occurring topics, key phrases, proximity terms, events, facts and trending popularity index. The disclosed embodiments may be performed via a wide variety of linking algorithms that can vary from simple conceptual distance measure to sophisticated graph clustering approaches based on the dimensions of the involved secondary features that aid in resolving a given extracted feature to a stored feature in the knowledge base. Additionally, embodiments can introduce an approach to evolves the existing feature knowledge base by a capability that not only updates the secondary features of the existing feature entry, but also expands it by discovering new features that can be appended to the knowledge base.

Embodiments of the disambiguation approach can employ a topic modeling approach to provide an automated weighted (across all the secondary features) linking process (disambiguation) that is modeled as topic inference. To support the automated weighted linking process, embodiments extend the conventional LDA topic modeling to build a novel topic modeling approach referred to as a multi-component LDA (MC-LDA) that can support any number of components (secondary features) as conditionally-independent. Embodiments of the modeling approach also can automatically learn the weights of components during training and employ them for inference (linking) in connection with disambiguation. The introduced MC-LDA approach for disambiguation can scale for any additional number of secondary features that could be introduced to increase disambiguation accuracy.

Figure 5:
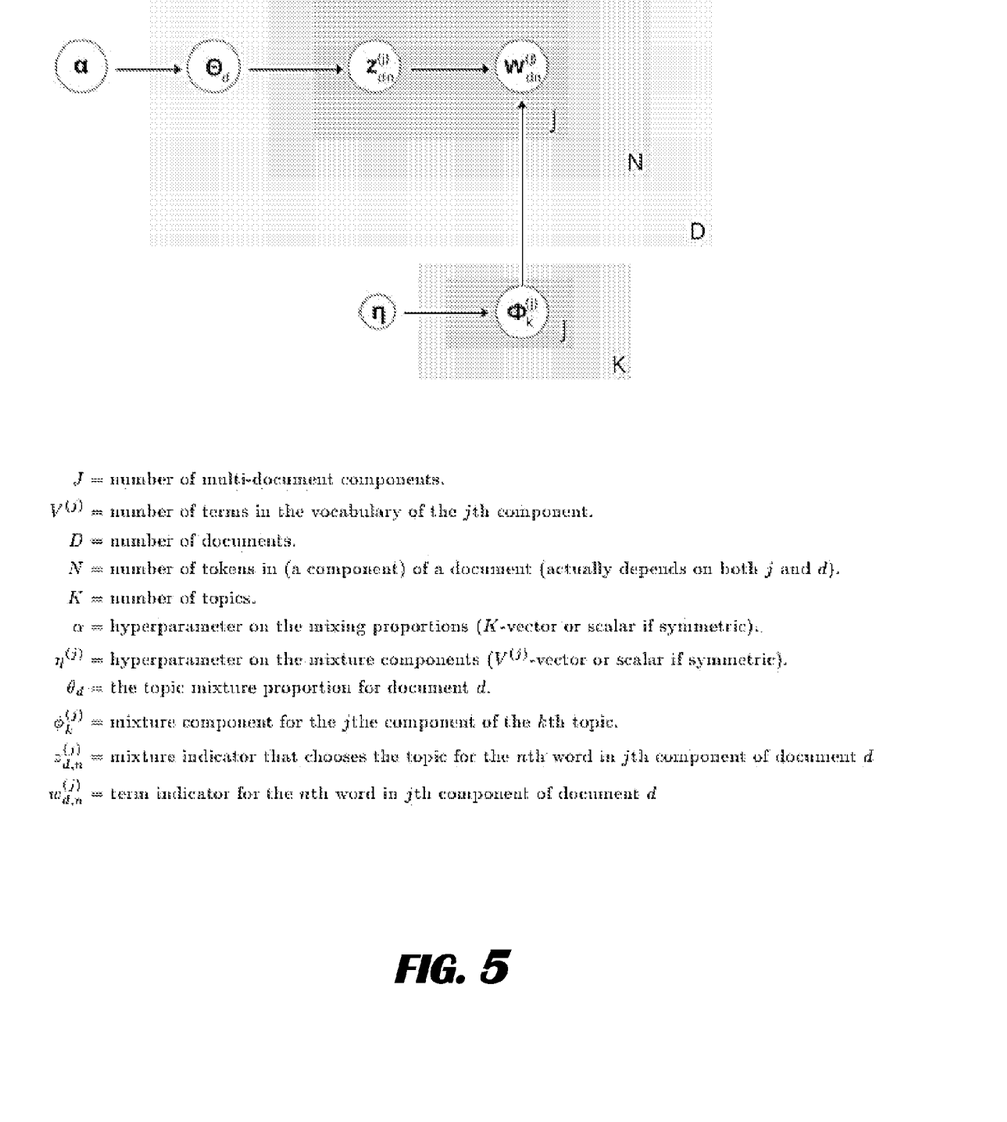
FIG. 5 shows a graphical representation of a multi-component, conditionally-independent Latent Dirichlet Allocation (MC-LDA) topic model, according to an exemplary embodiment.

FIG. 5 shows a graphical representation of an embodiment of a multi-component, conditionally-independent Latent Dirichlet Allocation (MC-LDA) topic computer modeling approach employed by system 400 of FIG. 4 above. In the illustrated embodiment, each component block represents modeling each secondary feature across the knowledge base, for instance as executed via the MemDB 408 of FIG. 4 that is initialized with the parameters set forth in FIG. 5.

Figure 6:
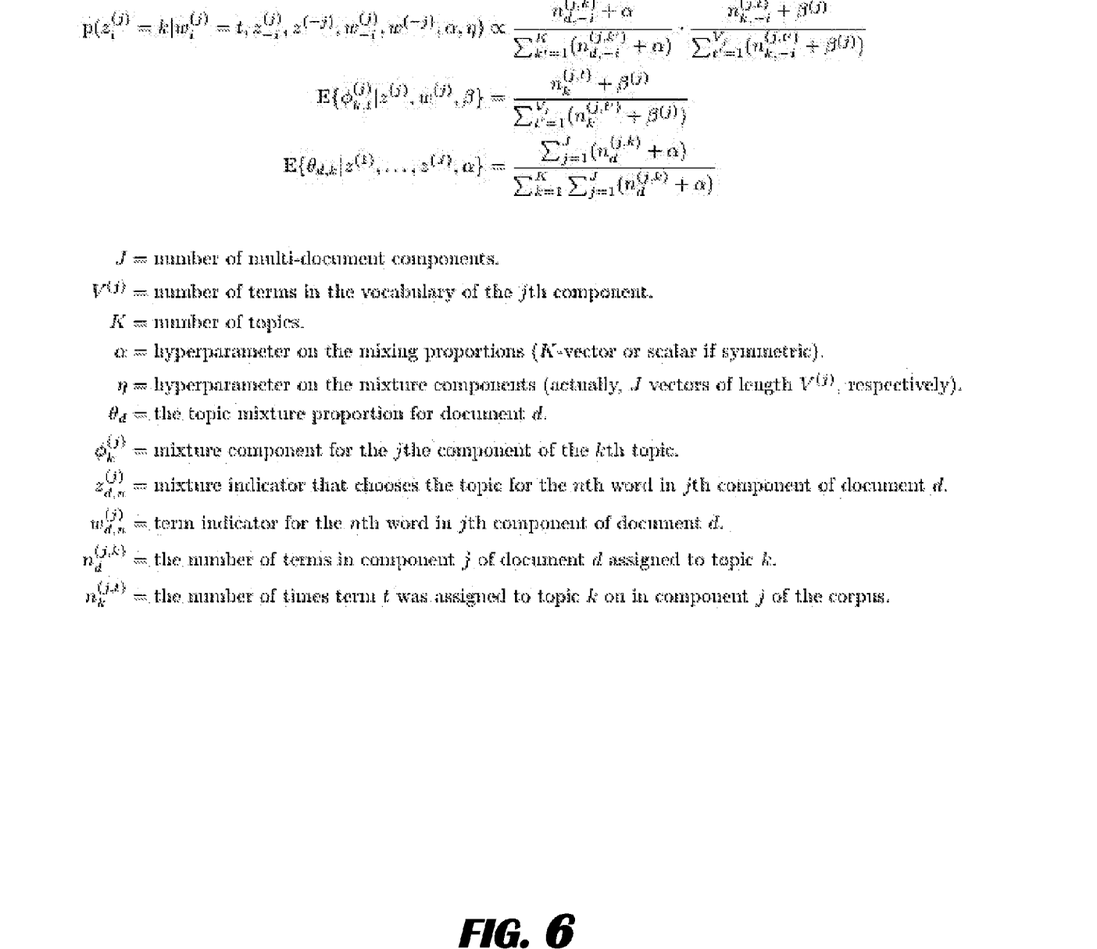
FIG. 6 illustrates an embodiment of the Gibbs sampling equations for multi-component, conditionally-independent latent Dirichlet allocation topic model, according to an exemplary embodiment.

FIG. 6 illustrates an embodiment of the Gibbs sampling equations for MC-LDA topic model employed in FIG. 5 above. An embodiment of this sampling approach aids the system 400 of FIG. 4 in training the individual component (secondary feature) weights in an automated fashion and in an efficient manner.

Figure 7:
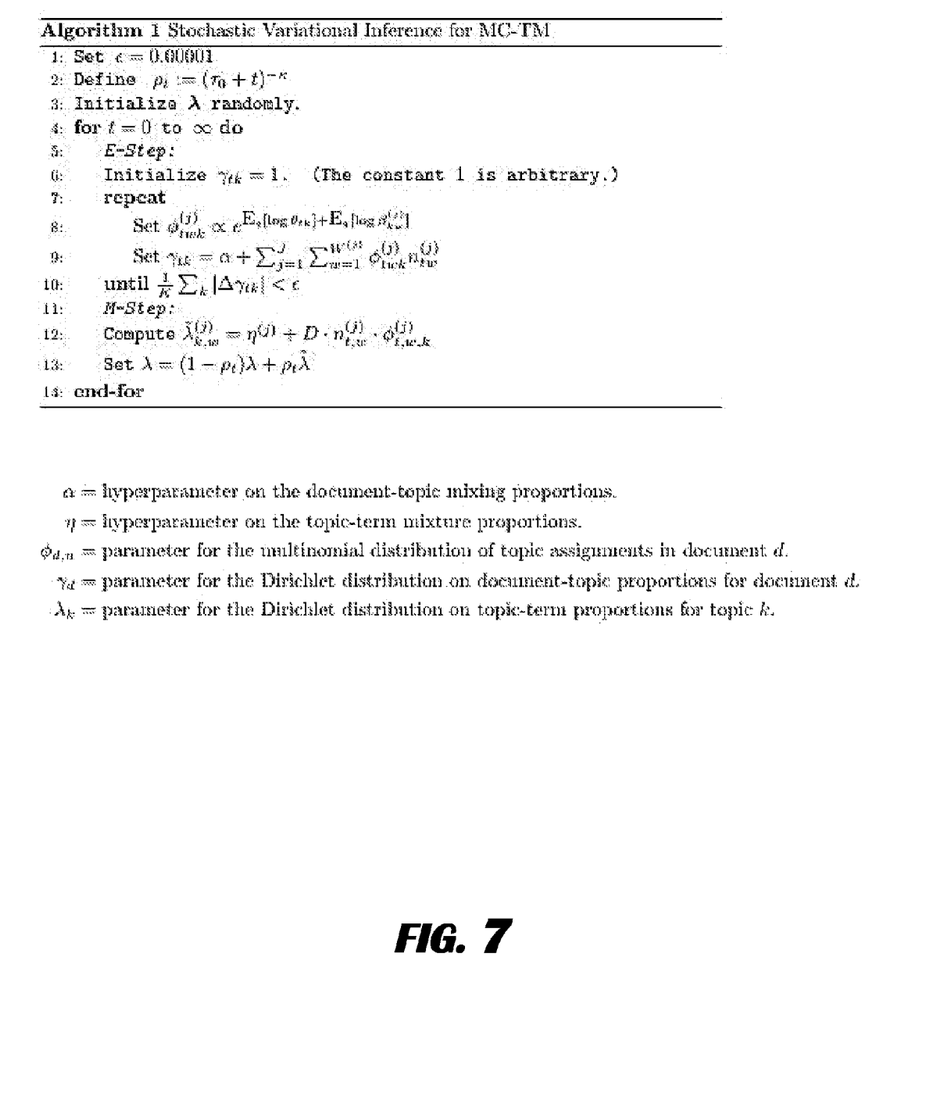
FIG. 7 illustrates an embodiment of the implementation of a stochastic variational inference algorithm for training and inference in multi-component, conditionally-independent latent Dirichlet allocation topic model, according to an exemplary embodiment.

FIG. 7 illustrates an embodiment of the computer executed implementation of a stochastic variational inference algorithm for training and inference in MC-LDA topic model of FIGS. 5-6, for instance as executed via the MemDB 408 of the system 400 of FIG. 4 that is initialized with the parameters set forth in FIG. 7. An embodiment of this inference method applies readily to model the linking/disambiguation process as topic inference, by taking all the secondary features (extracted from the document of interest) as an input and providing weighted topics as the output. These weighted topics can then be used to compute a similarity score against the stored feature knowledge base entries.

Figure 8:
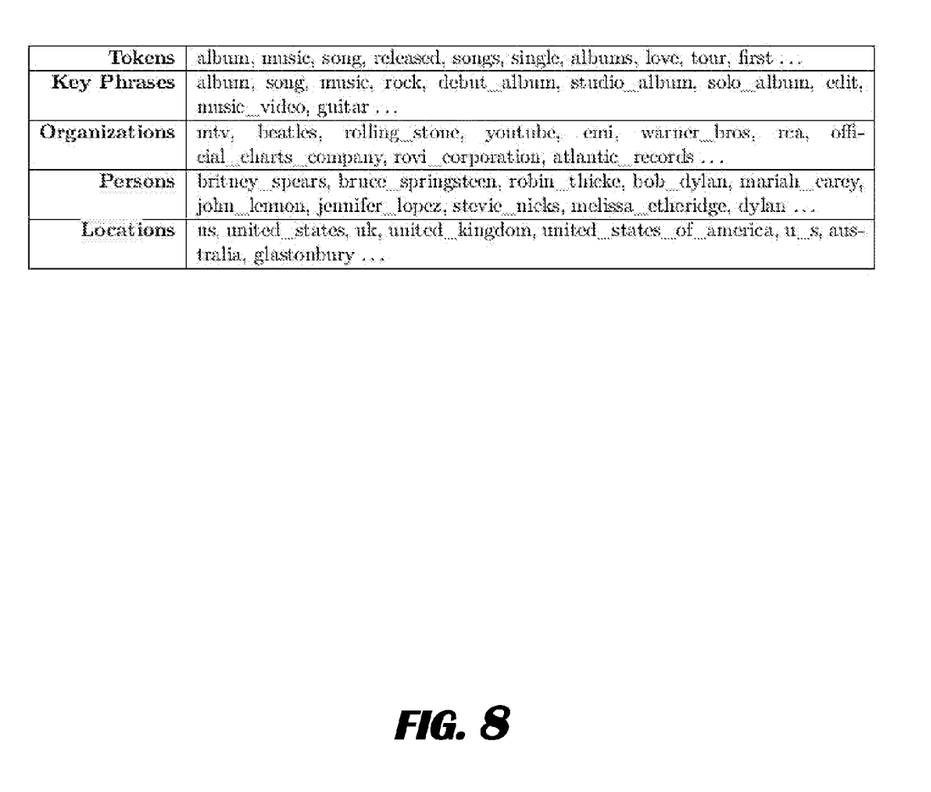
FIG. 8 is a table illustrating a sample topic for a multi-component, conditionally-independent latent Dirichlet allocation topic model, according to an exemplary embodiment.

FIG. 8 is a table illustrating a sample topic for a MC-LDA topic model. FIG. 8 displays the top scoring surface forms for each component of the model, for instance as executed via the MemDB 408 of the system 400 of FIG. 4, according to an embodiment.

Example #1 is an application of method 100 for disambiguating features in unstructured text, where the feature of interest (primary feature) is John Doe, a football player, and the user wants to monitor the news referencing John Doe. According to one embodiment, a document input 102 mentioning John Doe may be uploaded into the network. Features of document input 102 may be extracted and included into MemDB 408 for it to be disambiguated and linked to a cluster of secondary features associated to the primary feature (John Doe), and compared to existing cluster of similar features. Method 100 may output different feature IDs and the feature IDs' associated clusters that include all related secondary features to John Doe; for example, John Doe, engineer; John Doe, teacher; and John Doe, football player. Other primary features with similar secondary features may be considered, for example nicknames or short names. Then "JD" football player, from the same team as John Doe football player, with the same age and career may be considered the same primary feature. Therefore, all documents related to John Doe, football player, may be accessed easily.

Example #2 is an application of method 100 for disambiguating features in unstructured document, where the primary feature may be an image. According to one embodiment, method 100 may include a feature extraction 104, where a feature may be a general attribute, such as edges and shapes, among others; or a specific attribute, such as a tank, a person, and a clock, among others. For example, a new image may be input, where the image may have secondary features such as a specific shape (e.g., the shape of square, a person, or a car); the secondary features may be extracted and included in the MemDB 408 where a match may be found among all other images that has similar secondary features. According to the present embodiment, features may only include images, i.e. text may not be included as a feature.

Example #3 is an application of method 100 for disambiguating features in unstructured text, where the primary feature may be an event. According to one embodiment, when a query is made, method 100 may allow a user to receive results associated to an event, such as an earthquake, a fire, or an epidemic outbreak, among others. Method 100 may perform a feature extraction 104 and feature disambiguation 108 of the features to find the event's associated features and provide feature IDs of disambiguated features 110.

Example #4 is an embodiment of method 100, where prediction of one or more events that might occur may be made. According to one embodiment, a user may previously indicate features and events of interest prior to operation, and, therefore, links between different features associated to the events of interest may be previously established. As the associated features are appearing in the network in a high number of occurrences, method 100 may predict that the event of interest might occur, based on an increased number of occurrences of the associated features. When the imminent event is detected, an alert may be sent to the user. For example, a user working for the health department from Thailand may choose to receive an alert for an epidemic outbreak of dengue. As other users 406 from, for example, social networks upload comments including symptoms of dengue or inclusions into a hospital, method 100 may disambiguate all related comments from the social networks, and, taking in account the number of users 406 including related information, may predict and alert to the health department worker that an epidemic outbreak of dengue may be occurring. Therefore, the health department worker may have additional evidence and further actions may be taken into the affected community to keep the epidemic from spreading.

Example #5 is an application of method 100 for disambiguating features in unstructured text, where primary features may be geographic place names. According to an embodiment, method 100 may be employed to disambiguate the name of a city, where different scoring weights may be associated with secondary features in the disambiguation submodule. For example, method 100 may be employed to disambiguate Paris, Tex. from Paris, France.

Example #6 is an application of method 100 for disambiguating features in unstructured text, where primary features may be sentiments associated with a person, event, or company, among others; where sentiments may be positive or negative comments about a person, event, or company, among others, that may be fed from any suitable source, including social networks. According to one embodiment, method 100 may be employed for a company to acknowledge the acceptance that it is having amongst the public.

Example #7 is an embodiment of method 100, where method 100 may include human validation in order to increase the confidence score of a feature. According to one embodiment, link OTF process 300 (FIG. 4) may be assisted by a user, where the user may indicate if a disambiguated feature has been correctly disambiguated and indicate if two different clusters should be one, meaning that what method 100 (taking in account all feature and topic co-occurrence information) is indicating as two different primary features the user has knowledge may be the same. Therefore, the confidence score associated to that cluster may be higher, thus, the probability of the feature to be correctly disambiguated may be higher.

Example #8 is an embodiment of method 100 using disambiguation process 200 and link OTF process 300. In this example, the linking algorithm used in linking algorithm application 304 is configured to provide a confidence score above 0.85 within a period of 1000 ms.

Example #9 is an embodiment of method 100 using disambiguation process 200 and link OTF process 300. In this example, the linking algorithm used in linking algorithm application 304 is configured to provide a confidence score above 0.80 within a period of not exceeding 300 ms. The algorithm used in this example provides an answer in a smaller period of time compared to the algorithm used in example #8 but generally returns a lower confidence score.

Example #10 is an embodiment of method 100 using disambiguation process 200 and link OTF process 300. In this example, the linking algorithm used in linking algorithm application 304 is configured to provide a confidence score above 0.90 within a period of generally exceeding 3000 ms. The algorithm used in this example provides an answer with a confidence score generally greater than that returned by the algorithm used in example #8, but generally requires a significantly longer period of time.

Example #11 is an example of method 100 for disambiguating features in unstructured text to perform e-discovery on a large corpus of documents from a plurality of sources. Given a large corpus of documents from a plurality of sources, applying method 100 to disambiguate all features in those documents, enables the discovery of all features in the corpus. The collection of discovered features can be further utilized to discover all documents related to a feature and the discovery of related features.

The foregoing method descriptions and the process flow diagrams are provided merely as illustrative examples and are not intended to require or imply that the steps of the various embodiments must be performed in the order presented. As will be appreciated by one of skill in the art the steps in the foregoing embodiments may be performed in any order. Words such as "then," "next," etc. are not intended to limit the order of the steps; these words are simply used to guide the reader through the description of the methods. Although process flow diagrams may describe the operations as a sequential process, many of the operations can be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

The various illustrative logical blocks, modules, circuits, and algorithm steps described in connection with the embodiments disclosed here may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the invention. Thus, the operation and behavior of the systems and methods were described without reference to the specific software code being understood that software and control hardware can be designed to implement the systems and methods based on the description here.

When implemented in software, the functions may be stored as one or more instructions or code on a non-transitory computer-readable or processor-readable storage medium. The steps of a method or algorithm disclosed here may be embodied in a processor-executable software module which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used here, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

It is to be appreciated that the various components of the technology can be located at distant portions of a distributed network and/or the Internet, or within a dedicated secure, unsecured and/or encrypted system. Thus, it should be appreciated that the components of the system can be combined into one or more devices or co-located on a particular node of a distributed network, such as a telecommunications network. As will be appreciated from the description, and for reasons of computational efficiency, the components of the system can be arranged at any location within a distributed network without affecting the operation of the system. Moreover, the components could be embedded in a dedicated machine.

Furthermore, it should be appreciated that the various links connecting the elements can be wired or wireless links, or any combination thereof, or any other known or later developed element(s) that is capable of supplying and/or communicating data to and from the connected elements. The term module as used herein can refer to any known or later developed hardware, software, firmware, or combination thereof that is capable of performing the functionality associated with that element. The terms determine, calculate and compute, and variations thereof, as used herein are used interchangeably and include any type of methodology, process, mathematical operation or technique.

The preceding description of the disclosed embodiments is provided to enable any person skilled in the art to make or use the present invention. Various modifications to these embodiments will be readily apparent to those skilled in the art, and the generic principles defined here may be applied to other embodiments without departing from the spirit or scope of the invention. Thus, the present invention is not intended to be limited to the embodiments shown here but is to be accorded the widest scope consistent with the following claims and the principles and novel features disclosed here.

The embodiments described above are intended to be exemplary. One skilled in the art recognizes that numerous alternative components and embodiments that may be substituted for the particular examples described herein and still fall within the scope of the invention.

What is claimed is:

1. A method comprising:
in response to receiving a search query from an end user device:
searching, by a node of a system, a set of candidate records including co-occurring features to identify one or more candidate records matching one or more extracted features, wherein an extracted feature that matches a candidate record is a primary feature,
wherein the node comprises a main memory hosting an in-memory database, wherein the in-memory database stores a knowledge base of clusters, each cluster comprises a disambiguated primary feature with a unique identifier ("unique ID"), and a set of associated secondary features;
associating, by the node, each of the extracted features with one or more machine-generated topic identifiers ("topic IDs");
disambiguating, by the node, each of the primary features from one another based on relatedness of topic IDs;
identifying, by the node, a set of secondary features associated with each primary feature based upon the relatedness of topic IDs;
disambiguating, by the node, each of the primary features from each of the secondary features in the associated set of secondary features based on relatedness of topic IDs;
linking, by the node, in real-time, as data is retrieved from the knowledgebase from the in-memory database, each primary feature to the associated set of secondary features to form a new cluster;
determining, by a disambiguation module of the in-memory database of the node, whether each of the new cluster matches an existing knowledgebase cluster by assignment of relative matching scores to existing knowledge clusters with disambiguated primary features, wherein,
when there is a match, determining, an existing unique ID corresponding to each matching primary feature in the existing knowledgebase cluster and updating the existing knowledgebase cluster to include the new cluster;
when there is no match, creating, a new knowledgebase cluster and assigning a new unique ID to the primary feature of the new knowledgebase cluster; and
transmitting, one of the existing unique ID and the new unique ID for the primary feature to the user device.

2. The method according to claim 1, further comprising:
comparing, by the node, each of the candidate records matching an extracted feature; and assigning, by the node, a weighted match score result to each of the extracted features based upon the comparison.

3. The method according to claim 2, further comprising associating, by the node, each of the extracted features with a set of weighted feature attributes.

4. The method according to claim 3, further comprising determining, by the node, relatedness of each of the extracted features based on one or more weighted feature attributes.

5. The method according to claim 1, further comprising:
recognizing and extracting, by an extraction module of the node, one or more extracted features, wherein one or more primary features are identified in the one or more extracted features; and
storing, by the extraction module of the node, each of the extracted features in a database.

6. The method according to claim 5, further comprising assigning, by the extraction module of the node, an extraction certainty score to each of the features.

7. The method according to claim 1, wherein each primary feature is associated with a set of one or more feature attributes.

8. The method according to claim 7, wherein a feature attribute is selected from the group consisting of: a topic ID, a document identifier ("document ID"), a feature type, a feature name, a confidence score, and a feature position.

9. The method according to claim 1, wherein each associated feature is associated with a set of lower-ordinal features according to a pre-defined cluster hierarchy.

10. The method according to claim 1, further comprising performing, by a node, a fuzzy key search of the set of candidate records.

11. The method according to claim 7, further comprising linking, by a link-on-the fly module of the node, two or more data sources based on co-occurrence of related topic IDs and one or more feature attributes.

12. The method according to claim 1, further comprising:
determining, by the node, whether an extracted feature in a data source co-occurs in a second data source by comparing the extracted feature with a feature in the second data source; and linking, by the node, each of the data sources based upon the comparison.

13. The method according to claim 1, further comprising analyzing, by the node, co-occurrence of an extracted feature from different data sources to improve accuracy of disambiguating extracted features.

14. The method according to claim 1, further comprising:
continuously receiving, by the node, one or more new data sources;
continuously extracting, by the node, one or more extracted features;
continuously performing, by the node, candidate searching on the one or more extracted features;
continuously disambiguating, by the node, the extracted features; and
continuously linking, by the node, the extracted features into one or more new clusters.

15. A non-transitory computer readable medium having stored thereon computer executable instructions when executed by a processor performs functions comprising:
in response to receiving a search query from an end user device:
searching, by a node of a system, a set of candidate records including co-occurring features to identify one or more candidates records matching one or more extracted features, wherein the node comprises a main memory hosting the in-memory database,
wherein the node comprises a main memory hosting an in-memory database, wherein the in-memory database stores a knowledge base of clusters, each cluster comprises a disambiguated primary feature with a unique identifier ("unique ID"), and a set of associated secondary features;
associating, by the node, each of the extracted features with one or more machine-generated topic identifiers ("topic IDs");
disambiguating, by the node, each of the primary features from one another based on relatedness of topic IDs;
identifying, by the node, a set of secondary features associated with each primary feature based upon the relatedness of topic IDs;
disambiguating, by the node, each of the primary features from each of the secondary features in the associated set of secondary features based on relatedness of topic IDs;
linking, by the node, in real-time, as data is retrieved from the knowledgebase from the in-memory database, each primary feature to the associated set of secondary features to form a new cluster;
determining, by a disambiguation module of the in-memory database of the node, whether each of the new cluster matches an existing knowledgebase cluster by assignment of relative matching scores to existing knowledge clusters with disambiguated primary features, wherein,
when there is a match, determining, an existing unique ID corresponding to each matching primary feature in the existing knowledgebase cluster and updating the existing knowledgebase cluster to include the new cluster;
when there is no match, creating, a new knowledgebase cluster and assigning a new unique ID to the primary feature of the new knowledgebase cluster; and
transmitting, one of the existing unique ID and the new unique ID for the primary feature to the user device.

16. The non-transitory computer readable medium according to claim 15, wherein the instructions further comprise:
comparing, by the node, each of the candidate records matching an extracted feature; and
assigning a weighted match score result to each of the extracted features based upon the comparison.

17. The non-transitory computer readable medium according to claim 16, wherein the instructions further comprise associating, by the node, each of the extracted features with a set of weighted feature attributes.

18. The non-transitory computer readable medium according to claim 17, wherein the instructions further comprise determining, by the node, relatedness of each of the extracted features based on one or more weighted feature attributes.

19. The non-transitory computer readable medium according to claim 15, wherein the instructions further comprise:
recognizing and extracting, by an extraction module of the node, one or more extracted features, wherein one or more primary features are identified in the one or more extracted features; and
storing, by the extraction module of the node, each of the extracted features in a database.

20. The non-transitory computer readable medium according to claim 19, wherein the instructions further comprise assigning, by the extraction module of the node, an extraction certainty score to each of the features.

* * * * *